United States Patent
Bristow

(10) Patent No.: US 10,542,755 B2
(45) Date of Patent: Jan. 28, 2020

(54) AGROCHEMICAL COMPOSITION, METHOD FOR ITS PREPARATION AND USE THEREOF

(71) Applicant: ROTAM AGROCHEM INTERNATIONAL COMPANY LIMITED, Hong Kong (CN)

(72) Inventor: James Timothy Bristow, Hong Kong (CN)

(73) Assignee: ROTAM AGROCHEM INTERNATIONAL COMPANY LIMITED, Chai Wan (HK)

( * ) Notice: Subject to any disclaimer, the term of this patent is extended or adjusted under 35 U.S.C. 154(b) by 0 days.

(21) Appl. No.: 14/762,286

(22) PCT Filed: Nov. 26, 2013

(86) PCT No.: PCT/CN2013/087846
§ 371 (c)(1),
(2) Date: Jul. 21, 2015

(87) PCT Pub. No.: WO2014/110942
PCT Pub. Date: Jul. 24, 2014

(65) Prior Publication Data
US 2015/0373979 A1 Dec. 31, 2015

(30) Foreign Application Priority Data
Jan. 21, 2013 (GB) .................................. 1300994.9

(51) Int. Cl.
*A01N 43/80* (2006.01)
*A01N 25/28* (2006.01)
*B01J 13/14* (2006.01)
*A01N 43/00* (2006.01)
*A01N 25/00* (2006.01)

(52) U.S. Cl.
CPC .............. *A01N 43/80* (2013.01); *A01N 25/00* (2013.01); *A01N 25/28* (2013.01); *A01N 43/00* (2013.01); *B01J 13/14* (2013.01)

(58) Field of Classification Search
None
See application file for complete search history.

(56) References Cited

U.S. PATENT DOCUMENTS

| | | | |
|---|---|---|---|
| 4,285,720 A | 8/1981 | Scher | |
| 5,925,595 A * | 7/1999 | Seitz | A01N 25/28 424/405 |
| 6,218,339 B1 | 4/2001 | Becker et al. | |
| 6,380,133 B2 | 4/2002 | Becker et al. | |
| 6,387,385 B1 | 5/2002 | Wang | |
| 9,386,768 B2 * | 7/2016 | Bristow | A01N 43/40 |
| 2001/0041659 A1 | 11/2001 | Becker et al. | |
| 2002/0064656 A1 * | 5/2002 | Klug | B01J 13/14 428/402.21 |
| 2002/0086045 A1 | 7/2002 | Wang | |
| 2005/0271735 A1 * | 12/2005 | Stover | A01N 25/28 424/490 |
| 2007/0042182 A1 * | 2/2007 | Markus | A01N 65/00 428/402.2 |
| 2010/0248963 A1 | 9/2010 | Becher et al. | |
| 2011/0053776 A1 * | 3/2011 | Bahr | A01N 25/00 504/271 |

FOREIGN PATENT DOCUMENTS

| | | |
|---|---|---|
| CN | 1343092 A | 4/2002 |
| CN | 1383391 A | 12/2002 |
| CN | 102395277 A | 3/2012 |
| GB | 2496330 A | 5/2013 |
| WO | 0054590 A1 | 9/2000 |
| WO | 0196011 A1 | 12/2001 |

OTHER PUBLICATIONS

International Search Report PCT/CN2013/087846 dated Mar. 6, 2014.
Office Action from the State Intellectual Property Office of the People's Republic of China (CN201380047139.5), dated Apr. 21, 2016.
Extended European Search Report (EP 13 87 2160) and search opinion, dated Jul. 20, 2016.
Office Action from the Institut national de la propriétéindustrielle (FR1450073), dated Aug. 1, 2014.
Office Action from the Intellectual Property Office of the United Kingdom (GB1300994.9), dated May 22, 2015.
Office Action from the Intellectual Property Office of the United Kingdom (GB1300994.9), dated Nov. 24, 2015.
Office Action from the Taiwan Intellectual Property Office (TW103101905), dated Dec. 13, 2016.
(Continued)

*Primary Examiner* — Abigail Vanhorn
(74) *Attorney, Agent, or Firm* — Dickinson Wright PLLC

(57) ABSTRACT

A composition having an active compound contained within a microcapsule, the microcapsule having a wall comprising a polyurea formed by a polyisocyanate and a cross linking agent, the cross linking agent being the product of the reaction of a hydroxide salt with the copolymerization product of styrene and maleic anhydride. The active compound may be an agrochemical, in particular a herbicide or an insecticide. A process for the preparation of a microencapsulated active component including: providing an aqueous phase comprising a cross linking agent being the product of the reaction of a hydroxide salt with the copolymerization product of styrene and maleic anhydride; providing a first water-immiscible organic phase comprising an active ingredient to be encapsulated and a first polyisocyanate; dispersing the first organic phase in the aqueous phase; and allowing an interfacial polymerization reaction to occur at the interface of the organic phase and the aqueous phase to form a polyurea shell having the active component encapsulated therein.

20 Claims, No Drawings

(56) References Cited

OTHER PUBLICATIONS

Office Action from the State Intellectual property Service of Ukraine (Application No. a 201502355/MI-11338), dated Aug. 10, 2016.
Office Action from the State Intellectual Property Office of the People's Republic of China (CN201380047139.5), dated Jan. 10, 2017.

\* cited by examiner

AGROCHEMICAL COMPOSITION, METHOD FOR ITS PREPARATION AND USE THEREOF

This application is a 371 national phase entry of PCT/CN2013/087846, filed 26 Nov. 2013, which claims benefit of GB 1300994.9, filed 21 Jan. 2013, the entire contents of which are incorporated herein by reference for all purposes.

BACKGROUND

1. Field

The present disclosure relates to a composition, in particular a composition comprising a microencapsulated component. The composition finds particular use in the formulation of volatile components and is generally applicable, for example, to formulating agrochemical active ingredients. The present disclosure further relates to a method of preparing the same and, still further, to the use thereof.

2. Description of Related Art

Emulsifiable concentrate (EC) agricultural formulations of pesticides are well known in the art. These formulations are generally prepared by emulsifying and dispersing agents in addition to the pesticide to give a uniform composition. However, these agricultural formulations suffer numerous drawbacks because they are liquid. In particular, liquid pesticidal formulations must be handled carefully to minimize safety concerns, in particular dermal and ocular irritation. U.S. Pat. No. 6,387,388 contains a discussion of the drawbacks of such liquid formulations.

It is known in the art to microencapsulate pesticidal active compounds in a shell of polyurea. Unfortunately, these formulations do not provide optimum herbicidal efficacy when compared to the corresponding commercially available emulsifiable concentrate formulations. Many studies have shown that, in practice, the release rate of the active ingredient from the microcapsules is directly linked to the efficacy of the formulation in the field. It is well known in the art that the release rate of the active ingredient from the microcapsules is controlled by such factors as microcapsule size, degree of cross-linking, choice of polymer type, wall thickness and mobility of the oil phase.

U.S. Pat. No. 4,285,720 discloses a process for the production of microcapsules. The techniques disclosed provide for the production of microcapsules which are uni-modal in terms of wall thicknesses, and size. However, if microcapsules of differing modalities are desired, an entirely separate reaction would have to be conducted. It would be advantageous to provide microcapsules of differing dimensions and wall thicknesses.

U.S. Pat. No. 6,380,133 discloses a technique to encapsulate clomazone in polymer shell, with the polymer shell incorporating cross-linking of the polymer chains. However, control of the release rate of clomazone is still not satisfactory. An improved formulation for encapsulating volatile components, such as clomazone, is therefore needed.

SUMMARY

It has now been found that significant improvements in the performance of microencapsulated formulations may be obtained if the polymer shell of the microcapsules comprises a cross linking agent derived from the copolymerization product of styrene and maleic anhydride. Accordingly, an embodiment of the invention is directed to compositions, such as agrochemical formulations, comprising microcapsules, for example suspended in an aqueous liquid medium, wherein the microcapsules comprise a polyurea wall or shell containing therewithin an active ingredient, and a cross linking agent of the aforementioned type. The formulation is most suitably a suspension formulation, in which the microcapsules are suspended in a liquid medium, in the presence of necessary adjuvants, such as surfactants, as required for stability of the suspension.

According to an embodiment of the invention, there is provided, in a first aspect, a composition comprising an active compound contained within a microcapsule, the microcapsule having a wall comprising a polyurea formed by a polyisocyanate and a cross linking agent, the cross linking agent being the product of reacting a hydroxide salt with the copolymerization product of styrene and maleic anhydride.

The composition of an embodiment of the invention comprises microcapsules containing one or more active ingredients. The microcapsules have a shell or wall formed by the interfacial condensation reaction of a polyisocyanate in the presence of a cross-linking agent. In a preferred embodiment of this invention, the composition comprises a first microcapsule having a wall comprising a first polyisocyanate and a second microcapsule having a wall comprising a second polyisocyanate, wherein the second polyisocyanate is different from the first polyisocyanate.

The polymer shell of the microcapsules comprises a polyurea and a cross linking agent. The cross linking agent is preferably a resin derived from the copolymerization product of styrene and maleic anhydride, optionally in the presence of an alcohol. The copolymerization of styrene and maleic anhydride provides a non-esterified or anhydride copolymer. When the copolymerization of styrene and maleic anhydride is conducted with an alcohol, the maleic anhydride rings open to form a copolymer that is a half-acid and a half-ester of the corresponding alcohol present in the copolymerization reaction medium.

Such alcohols suitable for inclusion in the reaction medium include, without limitation, straight or branched chain alcohols, preferably alkyl alcohols. Suitable alcohols may have from 1 to 20 carbon atoms, more preferably from 1 to 12 carbon atoms, still more preferably from 1 to 8 carbon atoms. Lower alcohols, that is alcohols having from 1 to 6 carbon atoms are particularly preferred, especially $C_1$-$C_6$ alkyl alcohols.

The anhydride copolymers or the half acid/half ester copolymers are further reacted with hydroxides to provide the aforementioned resins. Suitable hydroxides are well known and are commonly available, such as ammonium hydroxide, and hydroxides of Group I or Group II of the Periodic Table, in particular sodium hydroxide, potassium hydroxide, magnesium hydroxide, calcium hydroxide, and the like. The hydroxides react with the aforementioned copolymers to provide the aforementioned resins in the form of water-soluble salts.

Reaction of the aforementioned hydroxides with the anhydride copolymer causes the maleic anhydride rings to open to provide a di-salt of the cation of the hydroxide, for example, a di-sodium salt or a di-potassium salt. When the anhydride copolymer is reacted with, for example, ammonium hydroxide, the maleic anhydride rings open to provide an amide/ammonium salt.

In an embodiment of the invention, the emulsifier/cross-linking agent is preferably selected from the ammonium hydroxide, sodium hydroxide, potassium hydroxide, magnesium hydroxide, and calcium hydroxide salts of an anhydrous copolymerization product of styrene and maleic anhydride; and the ammonium hydroxide, sodium hydroxide, potassium hydroxide, magnesium hydroxide, and calcium hydroxide salts of a half-acid/half-ester copolymerization product of styrene and maleic anhydride in the presence of an alcohol; and mixtures thereof. Particularly preferred resins are the ammonium hydroxide and sodium hydroxide salts of an anhydrous copolymerization product of styrene and maleic anhydride, most preferred is the ammonium hydroxide salt.

As noted above, the microcapsules of the composition of an embodiment of the invention comprise a polyurea wall or shell, containing therewithin one or more active components. The polyurea is formed by the reaction of a polyisocyanate. The reaction is conducted in the presence of the aforementioned cross linking resin, which is incorporated into the polymer to cross link the polyurea chains.

In a further aspect, the invention provides a process for the preparation of a microencapsulated active component, the process comprising:
  providing an aqueous phase comprising a cross linking agent being the product of the reaction of a hydroxide salt with the copolymerization product of styrene and maleic anhydride;
  providing a first water-immiscible organic phase comprising an active ingredient to be encapsulated and a first polyisocyanate;
  dispersing the first organic phase in the aqueous phase; and
  allowing an interfacial polymerization reaction to occur at the interface of the organic phase and the aqueous phase to form a polyurea shell having the active component encapsulated therein.

In a preferred embodiment of this invention, the process further comprises providing a second water-immiscible organic phase comprising an active ingredient to be encapsulated and a second polyisocyanate; and dispersing the second organic phase in the aqueous phase.

In particular, an embodiment of the invention also provides a process of encapsulating water-immiscible material within discrete capsules of polyurea without addition of a second reactant. In this process, hydrolysis of an isocyanate monomer is used to form an amine, which in turn reacts with another isocyanate monomer to form polyurea. By conducting these reactions in the presence of the salt of the copolymerization product of styrene and maleic anhydride, optionally in the presence of an alcohol, the salt acts as a cross linking agent in the polyurea, thereby improving its properties.

In one particular embodiment, the process comprises the steps of:
  (a) providing at room temperature a dispersion of
    (i) a water-immiscible phase comprising the water-immiscible material to be encapsulated and an organic polyisocyanate in
    (ii) an aqueous phase comprising a solution of water, a surfactant and a protective colloid; and
    (iii) an effective amount of cross-linking resin selected from the group consisting of ammonium hydroxide, sodium hydroxide, potassium hydroxide, magnesium hydroxide, and calcium hydroxide salts of an anhydrous copolymerization product of styrene and maleic anhydride; and the ammonium hydroxide, sodium hydroxide, potassium hydroxide, magnesium hydroxide, and calcium hydroxide salts of a half acid/half ester copolymerization product of styrene and maleic anhydride in the presence of an alcohol; and (b) heating and maintaining the dispersion in a temperature range of about 40° C. to about 90° C., whereupon the water-immiscible material is encapsulated within discrete polyurea capsule enclosures directly usable without further separation or purification, the improvement comprising providing a plurality of water-immiscible phases each comprising at least one individually distinct wall-forming organic polyisocyanate monomer, and a water-immiscible material to be encapsulated in a polyurea wall formed from said polyisocyanate monomer, and sequentially or simultaneously dispersing each of said water-immiscible phases in the aqueous phase.

DETAILED DESCRIPTION OF SPECIFIC EMBODIMENTS

The invention, in an embodiment, employs a polyisocyanate to form a polyurea microcapsule. The polyisocyanates used as starting components according to the invention may be aliphatic, cycloaliphatic, araliphatic, aromatic or heterocyclic polyisocyanates such as those described, for example, by W. Siefken in Justus Liebigs Annalen der Chemie, 562, pages 75 to 136. Suitable isocyanates include diisocyanates and higher polyisocyanates. Examples of suitable isocyanates include ethylene diisocyanate; tetramethylene-1,4-diisocyanate; hexamethylene-1,6-diisocyanate; dodecane-1,12-diisocyanate; cyclobutane-1,3-diisocyanate; cyclohexane-1,3- and 1,4-diisocyanate and any mixtures of these isomers; 1-isocyanato-3,3,5-trimethyl-5-isocyanatomethylcyclohexane (as disclosed, for example in DE 1,202,785 and U.S. Pat. No. 3,401,190); hexahydrotolylene-2,4-diisocyanate and -2,6-diisocyanate and any mixtures of these isomers; hexahydrophenylene-1,3-diisocyanate and/or 1,4-diisocyanate; perhydrodiphenyl methane-2,4'-diisocyanate and/or 4,4'-diisocyanate; phenylene-1,3-diisocyanate and -1,4-diisocyanate; tolylene-2,4-diisocyanate and -2,6-diisocyanate and any mixtures of these isomers; diphenylmethane-2,4'-diisocyanate and/or 4,4'-diisocyanate; naphthylene-1,5-diisocyanate; triphenylmethane-4,4',4"-triisocyanate; polyphenylpolymethylene polyisocyanates which can be obtained by aniline/formaldehyde condensation followed by phosgenation, as described, for example, in GB 874,430 and GB 848,671;

m- and p-isocyanatophenylsulphonyl-sulphonyl isocyanates, as described in U.S. Pat. No. 3,454,606; perchlorinated aryl polyisocyanates such as those described, for example, in U.S. Pat. No. 3,277,138; polyisocyanates having carbodiimide groups as described in U.S. Pat. No. 3,152,162; diisocyanates of the kind described in U.S. Pat. No. 3,492,330; polyisocyanates with allophanate groups as described, for example in GB 994,890, BE 761,626 and NL 7,102,524; polyisocyanates with isocyanate groups, for example as described in U.S. Pat. No. 3,001,973, DE 1,022,789, DE 1,222,067 and DE 1,027,394, DE 1,929,034 and DE 2,004,048; polyisocyanates with urethane groups as described for example in BE 752,261 or U.S. Pat. No. 3,394,164; polyisocyanates with acylated urea groups as described in DE 1,230,778; polyisocyanates with biuret groups as described for example in U.S. Pat. Nos. 3,124,605 and 3,201,372, and GB 889,050; polyisocyanates prepared by telomerization reactions as described, for example, in U.S. Pat. No. 3,654,106; polyisocyanates having ester groups such as those described, for example, in GB 965,474 and GB 1,072,956, U.S. Pat. No. 3,567,763 and DE 1,231,688; reaction products of the above mentioned isocyanates with acetals as described in DE1,072,385; and polyisocyanates containing polymeric fatty acid groups as described in U.S. Pat. No. 3,455,883.

The distillation residues obtained from the commercial production of isocyanates which contain isocyanate groups may also be used, optionally as solutions in one or more of the above mentioned polyisocyanates. Any mixtures of the above mentioned polyisocyanates may also be used.

As a general rule, it is particularly preferred to use readily available polyisocyanates such as tolylene-2,4-diisocyanate and -2,6-diisocyanate and any mixtures of these isomers ("TDI"); polyphenyl-polymethylene polyisocyanates of the kind which can be prepared by aniline/formaldehyde condensation followed by phosgenation ("crude MDI"); and polyisocyanates containing carbodiimide groups, urethane groups, allophanate groups, isocyanurate groups, urea groups or biuret groups ("modified polyisocyanates").

Each polyisocyanate is an individual wall-forming monomer. A single polyisocyanate or a combination of two or more different polyisocyanates may be used. If two or more distinct polyisocyanates are used, capsules of different properties, in particular wall thicknesses and wall compositions, can be produced, depending upon the type and amount of polyisocyanates employed.

The nature of the organic polyisocyanates employed determines the release properties of the capsules formed by this process. The selection of polyisocyanates also determines the structural physical strength of the capsular skin. The organic polyisocyanates contemplated in this process include those members of the aromatic polyisocyanate class which includes the aromatic diisocyanates, the aliphatic diisocyanate class, high molecular weight linear aliphatic diisocyanates and the isocyanate pre-polymers. Representative of the aromatic diisocyanates and other polyisocyanates are the following: 1-chloro-2,4-phenylene diisocyanate, m-phenylene diisocyanate, p-phenylene diisocyanate, 4,4'-methylenebis(phenyl isocyanate), 2,4-tolylene diisocyanate, tolylene diisocyanate (60% 2,4-isomer, 40% 2,6-isomer) 2,6-tolylene diisocyanate, 3,3'-dimethyl-4,4'-diphenylene diisocyanate, 4,4'-methylenebis(2-methylphenyl isocyanate), 3,3'-di-methoxy-4,4'-biphenylene diisocyanate, 2,2',5,5'-tetramethyl-4,4'-bi-phenylene diisocyanate, 80% 2,4- and 20% 2,6-isomer of tolylene diisocyanate and polymethylene polyphenyl isocyanate (PAPI). It is highly desirable to use combinations of the above-mentioned organic polyisocyanates. Such combinations as, for example, polymethylene polyphenyl isocyanate and tolylene diisocyanate, containing 80% 2,4- and 20% 2,6-isomers, produce excellent capsular enclosures with exceptional controlled release properties.

The amount of organic polyisocyanate used in the process will determine the wall content of the capsules formed therein. Generally, based on each of the organic phases, there will be greater than about 2% by weight organic polyisocyanate present. However, this is by no means limiting and a greater amount can be used that is approaching 100%. Clearly, 100% would not be entirely desirable since this would result in a product with no encapsulated material. The preferred range is from about 2% to about 75% by weight of organic polyisocyanate, thereby forming an encapsulated product having a corresponding wall content, that is, about 2% to about 75% by weight. More particularly, the preferred range is from about 5% to about 50% by weight of isocyanate in the microcapsule wall.

In all other respects the process may be the same as that described in U.S. Pat. No. 4,285,720, with all of the limitations therein with respect to process conditions. In all cases, within the practice of the invention, a preferred procedure involves first, producing, for example by simple agitation, a solution of water, a suitable surfactant and a protective colloid. These three ingredients comprise the aqueous phase or continuous phase of the process. The aqueous or continuous phase is essentially free of any components that will react with the material therein or any of such group of materials. The surfactant and protective colloid in the aqueous phase do not enter into the polycondensation reaction by which the capsule wall is formed.

By way of further example, the surfactants in the aqueous or continuous phase can be described as nonionic, anionic or cationic surfactants, preferably in the HLB (hydrophile-lipophile balance) range from about 12 to about 16. There are many surfactants which satisfy this HLB range requirement. Among the acceptable surfactants are sodium isopropyl naphthalene sulfonate, polyoxyethylenesorbitol oleate laurate, ethoxylated nonylphenols. However, the preferred surfactant is of the class of polyethylene glycol ethers of linear alcohols. Whereas the surfactant is described herein as placed in the aqueous phase, it can also be placed in the organic phase or phases. Without specific reference to the phase in which the surfactant is placed, there will be a partitioning and distribution of the surfactant between each phase upon the mixing of the phases depending upon the relative solubility therein. The use of a surfactant may be omitted provided that a sufficiently high shear rate is employed to form the dispersion. In the preferred embodiment of this invention a surfactant is employed.

The range of surfactant concentration found most acceptable in this system is from about 0.01% to about 3.0% by weight based on the aqueous phase. Higher concentrations of surfactant may be used, however without necessarily increasing the ease of dispersibility.

A protective colloid may also be present in the aqueous or continuous phase, which can be selected from a wide range of such materials. The usable protective colloids are exemplified by the following: polyacrylates, methyl cellulose, polyvinyl alcohol, polyacrylamide poly(methylvinyl ether/maleic anhydride) and polymeric lignin sulfonates. Such colloids are known in the art.

The amount of colloid employed will depend upon various factors such as molecular weight, type and effectiveness within the media, compatibility with other components of the system, and the like. The colloid may be added at any suitable time in the process. It has been found that the protective colloid can be added to the aqueous phase prior to addition of the organic phases or following the dispersion thereof. As another alternative, a portion of the protective colloid may be added prior to addition of the organic phases and the remaining colloid after the dispersion step. Generally, the amount of colloid employed will be in the range of from about 0.1% to about 5% by weight, based on the aqueous phase.

Each of the other phases, known as the organic phases, comprises the material to be encapsulated, and at least one polyisocyanate, each polyisocyanate being an individually wall-forming monomer. The material to be encapsulated can be used in a concentrated form or in solution in a water-immiscible solvent. The process may employ a single organic phase containing one or more polyisocyanates. Alternatively, the process may employ a plurality of organic phases, for example two or more organic phases, each organic phase containing one or more polyisocyanates. Each of the organic phases is preferably separately dispersed in the continuous aqueous phase, whereby each dispersed organic phase forms microcapsules, the properties and composition of which are determined by the number and type of the polyisocyanates contained in that organic phase.

The material to be encapsulated can be used as the solvent for the one or more polyisocyanates. However, to achieve a desired concentration of active material in the final product, a water immiscible organic solvent is preferably used, to dissolve the material to be encapsulated and the polyisocyanate.

The organic phases containing the material to be encapsulated and the polyisocyanate may be added simultaneously to the aqueous phase. Separate phases may also be added sequentially, if desired. If two or more separate organic phases are employed and are added sequentially, preferably, the phases are added sequentially but close together, one after the other. Each phase of the material to be encapsulated and the polyisocyanate are pre-mixed to obtain a homogeneous phase before addition to and mixing with the aqueous phase.

The total amount of the organic phases may vary from about 1% to about 75% by volume of the aqueous phase present in the reaction vessel. The concentrations in the lower end of the range are relatively undesirable since they result in a very dilute suspension of capsules. The preferred total amount of organic phase is from 10 to 60% by volume, more preferably from about 25% to about 50% by volume.

In accordance with preferred practice of an embodiment of the invention, the following general steps comprise the process which utilizes the substantially immiscible phases described above. In general, the process comprises establishing a physical dispersion of each of the organic phases in the aqueous or continuous phase, such dispersion thereby establishing droplets of the desired size in the aqueous phase. Thereafter, the desired condensation reaction is thereby effected at the interfaces between the droplets and the continuous phase, for example by adjusting the pH of the resulting mixture and the temperature within the appropriate temperature range. Certain variations in the sequence of steps between adjustment of the pH and addition of required heat will be apparent in the following discussion and examples.

The temperature of the multiple-phase mixture, that is, the dispersion of the organic phases in the aqueous phase, is typically raised to a suitable temperature for the condensation reaction at the liquid interface to occur. Suitable temperatures are typically in the range of from about 20° to 90° C., preferably from about 30° to 80° C., more preferably about 40° C. to about 60° C. The heat to initiate the reaction can be applied to the dispersion of the organic phase in the aqueous phase simultaneously or after the adjustment of the pH to the desired value. Alternatively, the aqueous phase can be heated to the required temperature prior to the steps of addition of the organic phases and their dispersion in the continuous aqueous phase. In this alternative procedure, the adjustment of the pH is preferably performed after the dispersion is accomplished and the pH is maintained within the limits to be discussed below.

In some embodiments of the invention, it may be preferred that a catalyst capable of increasing the rate of isocyanate hydrolysis, for example, the basic amine type, is added to each of the organic phases or aqueous phase prior to the initiation of the desired condensation reaction. The addition of a catalyst may be used as an alternative to heating the mixture. Alternatively, increased temperature and catalyst can be used simultaneously to effect the desired polycondensation reaction.

In embodiments employing a catalyst, the catalyst may be added at any suitable point in the procedure before the interfacial condensation reactions are initiated. The catalyst in such a procedure is preferably added to the organic phases and is added to the system at the time of mixing of the aqueous and each of the organic phases.

Various catalysts have been found acceptable for use in the process of the present invention and their selection will depend upon factors easily determinable by one skilled in the art. It has been found that certain basic organic amines, preferably the tertiary amines, and alkyl tin acetates such as tributyl tin acetate and di-n-butyl tin diacetate are acceptable catalysts. Included among the basic total organic tertiary amines are triethylene diamine, N,N,N',N'-tetramethyl-1,3-butane-diamine, triethylamine, tri-nbutylamine and the like. The amount of catalyst will vary with the particular system and conditions. When an alkyl tin acetate is used, about 0.001% to about 1% by weight based on the organic phase is employed. When a basic organic amine is used, about 0.01% to about 10% by weight based on the total of the organic phases is employed.

It has been found that water may be soluble in the water-immiscible material to be encapsulated. The amount of water which will be dissolved in the material to be encapsulated will depend upon the nature of the material. Usually the amount of water dissolved is relatively minor. However, when using a water-immiscible material that can dissolve an appreciable quantity of water, some deviation in the normal processes described herein is preferred. In such a system it has been found that particles with a poorly defined wall structure can result. Well-defined microcapsules can be prepared by adding an appropriate catalyst to the aqueous phase after the dispersion or emulsion is formed. Thereby, the bulk of the polymerization takes place at the interface where the catalyst is present. In such cases, it is preferred that the mixture is not heated, otherwise polymer will form not only on the surface of the microcapsules at the interface, but an increased proportion will form within the body of the water-immiscible material. As a result, the procedure is preferably performed at about room temperature (15° to 30° C.) in such cases.

The technique of adding the catalyst to the aqueous phase after dispersion is not limited to encapsulation of only water-immiscible material that can dissolve appreciable quantity of water, but finds general applicability with any water-immiscible material herein discussed and described.

It is satisfactory to prepare the aqueous phase as described above. While stirring the aqueous phase, the organic phases are added, preferably in a pre-mixed state. As previously stated, these organic phases can be added simultaneously or sequentially. Upon addition of the organic phases to the aqueous phase, a suitable dispersing means to disperse one liquid into the other is employed. Any high shear device can be used conveniently to obtain the desired particle size within the range of from about 0.5 microns to about 4,000 microns. The actual range of droplet sizes will depend upon the desired end use. As an example, the preferred range for most pesticidal applications is from about 1 micron to about 100 microns. In one embodiment each organic phase is dispersed in the continuous aqueous phase to a particle size in the range of from 5 to 60 microns, more preferably from 10 to 50 microns. The process of an embodiment of the invention is applicable to preparing widely varied but uniform sized capsules. Once the desired droplet size is obtained, the dispersion means employed to establish the desired droplet size is discontinued. Only mild agitation is required for the balance of the process, to maintain the dispersion of the organic liquid phase.

The process of an embodiment of the invention may be performed and encapsulated material produced without adjustment to a specific pH value. That is, no adjustment of the pH of the system needs to be made during the encapsulation process. The encapsulation process will proceed at a pH value of between about 0 to about 14. The desirability of any adjustment of pH to a particular value will depend upon such factors as the nature of the components in the system, such as surfactant, colloid, catalyst, temperature, material to be encapsulated and the like. For example, if the pH is allowed to drop below about 7.0, carbon dioxide will be liberated during the course of the reaction. If it is desirable to eliminate this evolution of carbon dioxide, then adjustment can be made to a pH value of at least about 7.0, preferably higher.

The pH of the system may be adjusted after dispersion and maintained at that value for the remainder of the condensation reaction. Alternatively, the adjustment of the pH can take place in the aqueous phase prior to the addition and dispersion therein of the organic phases. The adjustment and maintenance of a particular pH throughout the reaction can be accomplished by the addition of appropriate amounts of various water soluble bases or acids. As will be appreciated, such acids and bases should not react with other components of the system or with the polyisocyanate intermediates formed during the condensation reactions. Preferred compounds for adjusting the pH include inorganic acids and bases, for example concentrated sodium hydroxide (25% solution), potassium hydroxide, hydrochloric acid and the like.

As noted above, depending upon the nature of the reactions taking place, carbon dioxide may be produced. The evolution of carbon dioxide may cause considerable undesirable foam formation and/or volume expansion which may interfere with the processing of the reaction mixture. As noted above, the evolution of carbon dioxide may be reduced or prevented by the appropriate adjustment of the pH of the system. An alternative to the adjustment of the pH in order to eliminate the excessive foam produced by the carbon dioxide evolution is the addition of a defoamer. By using an appropriate defoamer, it is possible to satisfactorily produce the encapsulated material at an acidic pH without the addition of a base, such as caustic soda, to the acidic system. The defoamer may be added at any time to the processing mixture. Suitable defoamers are known in the art and are commercially available.

The desired condensation reaction at the interface between the droplets and the continuous phase occurs very rapidly, the majority of the reaction taking place within the first one-half hour of reaction time. In order to ensure near completion of the condensation reaction throughout the system, the reaction conditions are preferably continued for an extended period of time, in particular from about 2 to 3 hours. The reaction time may be shortened by appropriate selection of the reaction conditions and/or by the use of an appropriate catalyst, as discussed above.

At the end of the reaction period, the formation of a capsule wall has been completed, thereby encapsulating the organic material within a skin of the polycondensate product of the condensation reactions. An advantageous aspect of an embodiment of the invention, resides in the fact that for certain intended applications, no further separation or handling of the encapsulated material is required, that is, the product is directly usable. The encapsulated material thus produced can be used for various direct applications. Alternatively, the encapsulated product may be further processed, for examply by incorporating the material into other products.

The thickness or chemical composition of the capsule walls can be selected or controlled in various ways. For example, these properties can be affected by control of the reaction condition, by chemical selection, especially in the reaction forming the cross-linkage, which in turn is determined by the functionality of the polyisocyanate. The thickness of the capsule skin can also be altered by varying the amounts of reactants within the individual organic phases. One convenient mode of controlling the size of the capsule is adjustment of the speed of agitation, that is, in forming the initial dispersion of the organic phases, smaller capsules may be obtained by subjecting the system to higher shear forces, for example by applying higher speeds of agitation resulting in a greater shearing force.

The capsules produced in accordance with an embodiment of the invention can be utilized in the same or analogous manner as the products of encapsulation procedures known in the art. Such techniques for use of encapsulated product are known in the art. Thus, for example, encapsulated herbicides or insecticides can be incorporated in dispersions for application purposes, for controlled release of the encapsulated material at the desired locality.

Special utility is noted for the encapsulation of various volatile or unstable insecticides and herbicides. By using encapsulation of the active ingredient, premature volatilization or other deterioration of the material is avoided. Such encapsulation can also serve the purpose of retarding or delaying the time taken for the product to act at the locus of application. In this way, the timing of the action of the product may be adjusted, as desired. The controlled release of the aforementioned materials may be important for environmental protection and to achieve the proper effect of the active ingredient on the organism to be controlled, as well as decreasing the toxicity of the active ingredient on beneficial or desirable organisms.

As previously mentioned and illustrated by the examples hereinafter, the process for encapsulation of the instant invention provides capsules capable of controlling the release of encapsulated organic material. Representative and especially of importance are the process and capsules comprising as a constituent in the organic phases herbicides, in particular herbicides of the class thiocarbamate such as S-ethyl diisobutylthiocarbamate, S-ethyl N,N-di-propylthiocarbamate, S-ethyl hexahydro-1H-azepine-1-carbothioate, S-propyl N,N-dipropylthiocarbamate, S-ethyl ethyl-cyclohexylthiocarbamate, S-propyl butylethylthiocarbamate; organophosphorus compounds of the class organophosphono and phosphorothioates; and dithioates such as O-ethyl S-phenyl ethylphosphonodithioate, S-[(p-chlorophenylthio)methyl]O,O-di-methylphosphorodithioate, O,O-dimethyl O-p-nitrophenylphosphorothiaote, O,O-diethyl O-p-nitrophenylphosphorothiaote. Other preferred herbicidally active ingredients are the isoxazolidinones, in particular 3-isoxazolidinones, especially 2-[(2-chlorophenyl)methyl]-4,4-dimethyl-3-isoxazolidinone, commonly known as clomazone.

Capsules of compounds useful for plant disease control provide a route to long term control of disease using compounds generally regarded to have only short term effectiveness once applied at a locus. Similarly, herbicides, nematocides, insecticides, rodenticides and soil nutrients can be encapsulated with the same useful results. Chemicals used for seed treatment are also readily encapsulated by the process of the present invention. Other biological products can be encapsulated including: anthelmintics, lamphrey and slime control agents, algicides, swimming pool chemicals, miticides, acaracides, animal attractants, antiseptics, deodorants, disinfectants, mildewicides, and the like.

The material to be encapsulated utilizing the process of the instant invention can be of any type which is water-immiscible. The material need not consist of only one compound, but may be a combination of two or more various types of water-immiscible materials. For example, employing an appropriate water-immiscible material, such a combination is an active herbicide and an active insecticide. Also contemplated is a water-immiscible material to be encapsulated which comprises an active ingredient, such as an herbicide and an inactive ingredient such as a solvent or extender adjuvant.

Encapsulation of a solid material can be accomplished by this method by forming a solution of the solid material in an appropriate solvent; thereby normally solid water-immiscible materials can be encapsulated. For example, the insecticide N-(mercaptomethyl)phthalimide S—(O,O-dimethylphosphorodithioate), m.p. 72° C., can be encapsulated by first dissolving the solid in an appropriate solvent, such as a heavy aromatic naphtha solvent.

The process of an embodiment of the invention may be practiced in a batch or batch-like mode or in a continuous or continuous-like mode. When the invention is practiced in a manner resembling a batch process, all the various liquids and various reactants will be brought together and various steps determined by the proper time sequence into a single body of liquid within a single vessel. In the continuous mode of the inventive process, dispersion and agitation of the reacting phases may continuously be practiced at an appropriate rate to continuously form suitable dispersion of droplets in the continuous phase and the resulting dispersion supplied continuously to a reactor in which the pH can be adjusted and the appropriate heat applied to achieve the desired condensation reactions. With the continuous mode of operation, the proper rate for reaction may be obtained by selecting the appropriate conditions in the reaction zone.

The invention is further described, for illustrative purposes only, by the following examples.

EXAMPLE 1

A pre-mixed aqueous phase consisting of 5.00 grams of an aqueous 25% solution of styrene maleic anhydride copolymer amide/ammonium salt (emulsifier/cross-linking, Scripset 720, from Solutia, Springfield, Mass.), 1.00 gram of a 100% polydimethyl siloxane (anti-foam agent, Dow Corning 1520US, from Ashland Chemical; Cleveland, Ohio), and 0.36 gram of an acidic 1.15% solution of a mixture of 2-methyl-4-isothiazolin-3-ones (a microbial growth inhibitor, Legend MK, from Rohm and Haas; Ambler, Pa.) in about 195.10 grams of water was placed in a 1000 ml vessel. The aqueous phase was homogenized at high speed (about 7000 rpm) for 10 seconds in a Brinkmann Polytron PT6000 blender.

A pre-mixed organic phase consisting of 210.00 grams of technical clomazone (90% active ingredient), 84.00 grams of polymethylene polyphenyl isocyanate (wall-forming material, PAPI 27, from Dow Chemical; Midland, Mich.), and 24.00 grams of a solvent consisting of a mixture of $C_9$-$C_{15}$ aromatic hydrocarbons with a flash point of about 95° C. (petroleum based solvent, Aromatic 200, from Exxon; Houston, Tex.) was added to the aqueous mixture at ambient temperature, with continued agitation.

Thereafter, 24.00 grams of an aqueous 2% xanthum gum solution (thickener, Kelzan S from Kelco; Chicago, Ill.) was added to the formulation during a 15 minute period to promote the suspension of the microcapsules in water. To this mixture was then added 42.00 grams of urea (widely available) as an antifreeze agent. The pH of the formulation was then adjusted to about 7.6 by the addition of about 5.00 grams of acetic acid (Aldrich, Milwaukee, Wis.).

The resulting product comprised microcapsules in an aqueous suspension having the following properties:

Particle size: 10.0 microns (90%); Viscosity: 900 cP; and pH: 7.6.

EXAMPLES 2 and 3

Additional formulations were prepared in accordance with the general procedure set out in Example 1, with the components of the mixtures as set out in Table 1 below.

TABLE 1

| | Component | Example 1 | Example 2 | Example 3 |
|---|---|---|---|---|
| Aqueous phase | Crosslinker (g) | 5 | 12 | 15 |
| | Anti-foam (g) | 1 | 2 | 2 |
| | Water (g) | 195 | 205 | 204 |
| Organic phase | Isocyanate (g) | 84 | 70 | 80 |
| | Solvent (g) | 24 | 24 | 24 |
| | Clomazone (g) | 210 | 210 | 210 |
| post encapsulation components | Thickener (g) | 24 | 18 | 10 |
| | Antifreeze (g) | 42 | 60 | 50 |
| | pH adjust (g) | 5 | 3 | 2 |

EXAMPLE 4

Biological Testing

The biological efficacy of the products of Examples 1 to 3 was compared with that of a known formulation, using the following procedure:

Seeds of barnyardgrass, giant foxtail, green foxtail, shatter-cane, and velvetleaf were planted in a 25 cm×15 cm×7.5 cm fiber flat containing topsoil. Each species was planted as a single row in the flat, which contained five rows. There were four replicate flats of the aforementioned weed species for each rate of application of the formulation being tested.

Stock solutions of each of the formulations being tested were prepared by dispersing a sufficient amount of formulation to provide 0.0356 grams of active ingredient in 40 mL of water. From the stock solution 20 mL was removed and serially diluted with 20 mL of water to provide application rates of 0.25, 0.125. 0.0625, 0.0313, 0.0156, and 0.0078 kg a.i./ha. The solutions of test formulation for each rate of application were then sprayed onto the surface of the soil using a track-sprayer and a spray hood.

Flats were also sprayed as above with the same rates of a standard clomazone formulation sold as Command® Herbicide 4.0 Emulsifiable Concentrate (EC).

A similar procedure was used to test the prior art formulation of U.S. Pat. No. 5,783,520, for comparison purposes.

Untreated controls were also included in each test.

Upon completion of the spraying, the flats were placed in a greenhouse, where they were maintained for fourteen days. After this time, the test was visually evaluated for percent weed control. The percent weed control data for each formulation being tested and the standard Command Herbicide 4.0 EC formulation was subjected to regression analysis to determine the rate of application that would provide 85% weed control ($ED_{85}$) of each of the weed species. From these data the relative potency of the test formulation (the relative potency of the Command Herbicide 4.0 EC being 1.0) was determined using the following ratio:

$$\text{Relative Potency of Formulation} = \frac{\text{Potency of Formulation}}{\text{Potency of Command Herbicide}}$$

Wherein the Potency of Formulation is inversely proportional to $ED_{85}$ of the formulation, and Potency of Command Herbicide is inversely proportional to $ED_{85}$ of Command Herbicide.

The results are set out in Table 2 below.

TABLE 2

| Formulation | Formulation Relative Potency | | | | |
| --- | --- | --- | --- | --- | --- |
| | Barnyard-grass | Giant foxtail | Green foxtail | Shatter-cane | Velvet-leaf |
| Formulation 1 | 1.21 | 1.38 | 1.1 | 1.3 | 1.7 |
| Formulation 2 | 1.11 | 1.34 | 1.05 | 1.23 | 1.2 |
| Formulation 3 | 1.09 | 1.42 | 1 | 1.1 | 1.65 |
| Formulation U.S. Pat. No. 5,783,520 | 0.3 | 0.5 | 0.6 | 0.55 | 0.4 |
| Command Herbicide 4EC | 1 | 1 | 1 | 1 | 1 |

The formulations of Examples 1, 2 and 3 of the present invention are generally at least equal in herbicidal activity to the standard Command Herbicide 4EC and in many cases exhibit significantly improved herbicidal activity.

It is also to be noted that the formulations of Example 1 to 3 are significantly more herbicidally active than the comparative formulation of U.S. Pat. No. 5,783,520.

While the invention has been described in detail and with reference to specific embodiments thereof, it will be apparent to one skilled in the art that various changes and modifications can be made to the invention without departing from the spirit and scope thereof.

The invention claimed is:

1. A composition comprising clomazone contained within a first microcapsule, said first microcapsule having a wall consisting of a polyurea formed from a reaction mixture consisting of one or more polyisocyanates and a cross linking agent, wherein said polyurea is formed by hydrolysis of a portion of said one or more polyisocyanates and wherein said cross linking agent consists of the reaction products of a hydroxide salt with the copolymerization reaction products of a reaction mixture consisting of styrene, maleic anhydride and, optionally, an alcohol.

2. The composition according to claim 1, wherein the alcohol is an alkyl alcohol.

3. The composition according to claim 2, wherein the alcohol has from 1 to 6 carbon atoms.

4. The composition according to claim 1, wherein the hydroxide salt is ammonium hydroxide or a hydroxide of a metal from Group I or Group II of the Periodic Table.

5. The composition according to claim 4, wherein the hydroxide is selected from sodium hydroxide, potassium hydroxide, magnesium hydroxide and calcium hydroxide.

6. The composition according to claim 1, wherein the polyisocyanate is selected from 1-chloro-2,4-phenylene diisocyanate, m-phenylene diisocyanate, p-phenylene diisocyanate, 4,4'-methylenebis(phenyl isocyanate), 2,4-tolylene diisocyanate, tolylene diisocyanate (60% 2,4-isomer, 40% 2,6-isomer) 2,6-tolylene diisocyanate, 3,3'-dimethyl-4,4'-diphenylene diisocyanate, 4,4'-methylenebis(2-methylphenyl isocyanate), 3,3'-di-methoxy-4,4'-biphenylene diisocyanate, 2,2',5,5'-tetramethyl-4,4'-bi-phenylene diisocyanate, 80% 2,4- and 20% 2,6-isomer of tolylene diisocyanate and polymethylene polyphenyl isocyanate (PAPI), and mixtures thereof.

7. The composition according to claim 1 wherein the wall of microcapsule comprises from 2% to 75% by weight of polyisocyanate.

8. The composition according to claim 1, further comprising a second microcapsule, said second microcapsule having a wall consisting of a polyurea formed from a reaction mixture consisting of one or more polyisocyanates, said one or more polyisocyanates being different from said one or more polyisocyanates used to form said first microcapsule, and a cross linking agent, wherein said polyurea is formed by hydrolysis of a portion of said one or more polyisocyanates and wherein said cross linking agent consists of the reaction products of a hydroxide salt with the copolymerization reaction products of a reaction mixture consisting of styrene, maleic anhydride and, optionally, an alcohol.

9. A process for the preparation of the composition of claim 1, the process comprising: providing an aqueous phase comprising the cross linking agent; providing a first water-immiscible organic phase comprising the clomazone to be encapsulated and the one or more polyisocyanates; dispersing the first water-immiscible organic phase in the aqueous phase; and allowing an interfacial polymerization reaction to occur at the interface of the first water-immiscible organic phase and the aqueous phase to form the first microcapsule having the active component encapsulated therein.

10. The process according to claim 9, further comprising: providing a second water-immiscible organic phase comprising an active ingredient to be encapsulated and a second polyisocyanate; and dispersing the second water-immiscible organic phase in the aqueous phase.

11. process according to claim 9, wherein the organic phase is dispersed in the aqueous phase to a particle size of from 0.5 to 4,000 microns.

12. The process according to claim 11, wherein the organic phase is dispersed in the aqueous phase to a particle size of from 5 to 60 microns.

13. The process according to claim 9, wherein the organic phase further comprises a catalyst selected from: (a) a basic organic tertiary amine catalyst and (b) an alkyl tin acetate catalyst.

14. The process according to claim 13, wherein the basic organic tertiary amine catalyst is present in the amount of from 0.01 percent to 10.0 percent by weight based on the organic phase or the alkyl tin acetate catalyst is present in the amount of from 0.001percent to 1.0 percent by weight based on the organic phase.

15. The process according to claim 9, wherein the dispersed mixture further comprises a catalyst capable of increasing the rate of reaction of the one or more polyisocyanates to form the polyurea.

16. The process according to claim 15, wherein the catalyst is selected from a basic organic tertiary amine catalyst, an alkyl tin acetate catalyst, and mixtures thereof.

17. The process according to claim 9, wherein the organic phase further comprises a water-immiscible solvent.

18. The process according to claim 9, wherein the dispersed mixture is heated to a temperature in the range of from 20° to 90° C.

19. The process according to claim 9, wherein the pH of the dispersed mixture is adjusted to a pH in the range of at least 7.0.

20. A method for controlling organisms at a locus, comprising applying to the locus an effective amount of a composition according to claim 1.

* * * * *